United States Patent
Nirmalraj

(10) Patent No.: US 12,405,203 B2
(45) Date of Patent: Sep. 2, 2025

(54) DETECTION AND IMAGING OF AMYLOID AGGREGATES IN BLOOD

(71) Applicant: EMPA Eidgenössische Materialprüfungs-und Forschungsanstalt, Dübendorf (CH)

(72) Inventor: Peter Nirmalraj, Adliswil (CH)

(73) Assignee: EMPA Eidgenössische Materialprüfungs-und Forschungsanstalt, Dübendorf (CH)

( * ) Notice: Subject to any disclaimer, the term of this patent is extended or adjusted under 35 U.S.C. 154(b) by 449 days.

(21) Appl. No.: 17/926,621

(22) PCT Filed: May 18, 2021

(86) PCT No.: PCT/EP2021/063193
§ 371 (c)(1),
(2) Date: Nov. 20, 2022

(87) PCT Pub. No.: WO2021/233942
PCT Pub. Date: Nov. 25, 2021

(65) Prior Publication Data
US 2023/0184661 A1    Jun. 15, 2023

(30) Foreign Application Priority Data
May 19, 2020   (EP) .................................... 20175515

(51) Int. Cl.
*G01N 15/10*    (2024.01)
*G01N 1/36*    (2006.01)
(Continued)

(52) U.S. Cl.
CPC ........... *G01N 15/1023* (2024.01); *G01N 1/36* (2013.01); *G01Q 60/24* (2013.01); *G06T 7/0012* (2013.01);
(Continued)

(58) Field of Classification Search
CPC ................. G01N 15/1023; G01N 1/36; G01N 2015/012; G01N 2001/366;
(Continued)

(56) References Cited

U.S. PATENT DOCUMENTS

2005/0119187 A1*  6/2005  Hammer ............ C07K 14/4711
                                                              530/329
2022/0119468 A1*  4/2022  Moffet ..................... A61P 5/50

OTHER PUBLICATIONS

Yang C Y et al: "Observation of liquid/liquid interface by atomic force microscopy" Transducers 2009 : 2009 International Solid-State Sensors, Actuators and Microsystems Conference; Denver, Colorado, USA, Jun. 21-25, 2009, IEEE, Piscataway, NJ, USA, Jun. 21, 2009 (Jun. 21, 2009), pp. 2050-2053.
(Continued)

*Primary Examiner* — Nicole M Ippolito
(74) *Attorney, Agent, or Firm* — Renner, Otto, Boisselle & Sklar, LLP

(57) ABSTRACT

An aspect of the invention relates to a method for detecting amyloid aggregates (40) in blood. The method comprises providing a blood sample (20) comprising one or more red blood cells and performing an analysis of a surface layer (22) of the blood sample (20) by an atomic force microscope (10) to detect amyloid aggregates on the surface of the red blood cells and to image detected amyloid aggregates. Further aspects relate to a corresponding atomic force microscope and a corresponding computer program product.

21 Claims, 5 Drawing Sheets

(51) Int. Cl.
  *G01Q 60/24* (2010.01)
  *G06T 7/00* (2017.01)
  *G01N 15/01* (2024.01)

(52) U.S. Cl.
  CPC . *G01N 2001/366* (2013.01); *G01N 2015/012* (2024.01); *G01N 2015/1006* (2013.01); *G06T 2207/10056* (2013.01); *G06T 2207/30024* (2013.01)

(58) Field of Classification Search
  CPC ............ G01N 2015/1006; G01Q 60/24; G06T 7/0012; G06T 2207/10056; G06T 2207/30024
  See application file for complete search history.

(56) References Cited

OTHER PUBLICATIONS

David Perez-Guaita et al: "Multispectral Atomic Force Microscopy-Infrared Nano-Imaging of Malaria Infected Red Blood Cells" Analytical Chemistry, vol. 90, No. 5, Jan. 12, 2018 (Jan. 12, 2018), pp. 3140-3148.
Robert Nowakowski et al: "Imaging the surface details of red blood cells with atomic force microscopy" Surface and Interface Analysis., vol. 33, No. 2, Jan. 1, 2002 (Jan. 1, 2002), pp. 118-121.
International Search Report and Written Opinion for corresponding Application No. PCT/EP2021/063193 issued Jul. 26, 2021.
Cristiana Carelli-Ali Novi et al; "Morphological changes induced in erythrocyte by amyloid beta peptide and glucose depletion: A combined atomic force microscopy and biochemical study", BBA—Biomembranes, vol. 1861, No. 1. Jan. 1, 2019, pp. 236-244.
Francesco Ruggeri et al; "Identification of Oxidative Stress in Red Blood Cells with Nanoscale Chemical Resolution by Infrared Nanospectroscopy", International Journal of Molecular Sciences, vol. 19, No. 9, Aug. 30, 2018, p. 2582.

* cited by examiner

DETECTION AND IMAGING OF AMYLOID AGGREGATES IN BLOOD

This application is a national phase of International Application No. PCT/EP2021/063193 filed May 18, 2021, which claims priority to European Patent Application No. 20175515.4 filed May 19, 2020, each of which is hereby incorporated herein by reference in its entirety.

TECHNICAL FIELD

The present invention pertains to a method for detecting amyloid aggregates in blood.

Further aspects relate to a corresponding atomic force microscope and a computer program product for operating an atomic force microscope.

BACKGROUND ART

Amyloids are a class of proteins and/or peptides whose excessive aggregation has been associated with a plurality of human diseases denoted as amyloidosis and neurodegenerative disorders such as Alzheimer's disease and Parkinson's disease. Pathogenic amyloids may be formed from former healthy proteins if they lose their normal structure and physiological functions.

Positron emission tomography (PET) based imaging of the brain is currently the main route for detecting the abnormal accumulation of amyloid beta peptides responsible for the onset of Alzheimer's disease.

An alternative solution for a non-invasive detection of amyloids in blood is described in the document "High-precision plasma β-amyloid 42/40 predicts current and future brain amyloidosis", by Suzanne E. Schindler, James G. Bollinger, Vitaliy Ovod, Kwasi G. Mawuenyega, Yan Li, Brian A. Gordon, David M. Holtzman, John C. Morris, Tammie L. S. Benzinger, Chengjie Xiong, Anne M. Fagan, Randall J. Bateman; Neurology Oct 2019, 93 (17) e1647-e1659; DOI: 10.1212/WNL.0000000000008081. This is a two-tier based method for detecting amyloid aggregates.

In addition to the physical techniques available to detect amyloid aggregates the medium of detection is also important. Currently, neurodegenerative diseases are attempted to being diagnosed in the cerebral spinal fluid by PET analysis of amyloid oligomers using immunoassays and solid state nanopores. However, the problem with immunoassays and nanopore based approaches is that it is not possible to unambiguously detect all forms of amyloid aggregates starting from early stages of monomers to fibrillar aggregates in the advanced phase.

The document by Cristiana Carelli-Alinovi, Simone Dinarelli, Beatrice Sampaolese, Francesco Misiti and Marco Girasole, "Morphological changes induced in erythrocyte by amyloid beta peptide and glucose depletion: A combined atomic force microscopy and biochemical study, (BBA)—Biomembranes, Volume 1861, Issue 1,2019, Pages 236-244, ISSN 0005-2736, DOI: 10.1016/j.bbamem.2018.07.009", discloses that circulating red blood cells (RBCs) undergo aging. The document shows that treatment with beta amyloid peptide 1-42 (Aβ) accelerates the occurrence of morphological and biochemical aging markers in human RBCs and influences the cell metabolism leading to intracellular ATP depletion. The morphological pattern of the overall shape changes of erythrocytes has been monitored using Atomic Force Microscopy (AFM) imaging and measuring the RBCs' plasma membrane roughness employed as a morphological parameter capable to provide information on the structure and integrity of the membrane-skeleton.

DISCLOSURE OF THE INVENTION

Accordingly, one object of an aspect of the invention is to provide an advantageous method for detecting amyloid aggregates in blood.

According to an embodiment of a first aspect of the invention, there is provided a method for detecting amyloid aggregates in blood. The method comprises providing a blood sample. The blood sample comprises one or more red bloods cells, in particular a plurality of red blood cells. The method comprises performing an analysis of a surface layer of the blood sample by an atomic force microscope (AFM) to detect amyloid aggregates on a surface of the one or more red blood cells. The method further comprises imaging detected amyloid aggregates.

Hence embodiments of the invention facilitate the direct detection of amyloid aggregates in blood using a non-invasive approach, namely by means of atomic force microcopy. Furthermore, with such an embodied method the detection of amyloid aggregates in blood may be performed in an efficient and reliable way. According to embodiments of the invention, a surface layer of a blood sample is analyzed by imaging the surface by means of atomic force microscopy. The inventor of the present invention has discovered that such a surface analysis may already provide enough information to detect amyloid aggregates in the blood sample or in other words to detect the presence or absence of amyloid aggregates.

As amyloid aggregates are associated with a plurality of human diseases, methods according to embodiments of the invention may be used for the detection, in particular the early detection, of human diseases, in particular neurodegenerative diseases. According to embodiments, early stages of Alzheimers's disease and Parkinsons's disease may be detected.

According to embodiments the method may include at first a step of detecting amyloid aggregates on the surface of the red blood cells. Once an amyloid aggregate has been detected, the detected amyloid aggregate is then imaged and analyzed in more detail.

According to embodiments the analysis of the surface layer may encompass in particular quantifying the size, shape and/or the morphology of detected amyloid aggregates. This may be done according to embodiments on a nanometer scale.

According to embodiments the method may comprise detecting and imaging detected amyloid aggregates with varying size and shapes.

This includes the detection of spherical oligomers as well as the detection of cylindrical and elongated fibrils and protofibrils. Protofibrils are structures with spherical particles arranged in a linear chain. Such information may be used for developing targeted therapeutics to reduce amyloid plaques in human brains.

Embodiments of the invention allow in particular the detection of amyloid peptides including tau proteins and alpha-synucleins.

Methods according to embodiments of the invention may be field deployed and may be faster when compared to currently available multi-step processes. According to embodiments, the time period from the preparation of the blood sample until data extraction may be performed within approximately 30 to 45 minutes.

Methods according to embodiments of the invention may include resolving one or more geometric parameters of detected amyloid aggregates. Such geometric parameters may be generally any suitable parameters of interest and in particular parameters that may be an early indicator for a neurodegenerative disease. According to embodiments the one or more geometric parameters may encompass the size, shape and/or morphology of detected amyloid aggregates.

The step of resolving the one or more geometric parameters may involve a quantification of the one or more geometric parameters on a nanometer scale.

This may encompass according to embodiments a lateral resolution, i.e. a resolution in the x-y plane (see FIGS. 1-4 and 6a-6d), of up to 0.5 nm. This allows according to embodiments to resolve typical amyloid aggregates. According to embodiments the detected aggregates may encompass oligomeric aggregates (spherical particles) with a size span (maximum extension) between 3 nm to 15 nm. According to embodiments the detected aggregates may encompass single fibrils with a diameter from 6 to 15 nm (size derived from height profile) and a length from 200 nm to a few microns.

Hence methods according to embodiments of the invention may detect a full spectrum of size distribution of amyloid aggregates. This may include the detection and imaging of monomers, oligomers, protofibrils to fibrils. The overall size or in other words the maximum extension of the detected aggregates in one direction may range from 0.5 nm to several microns.

According to embodiments, the lateral resolution may be defined as the shortest distance between two points that can be differentiated by the observer or a camera system or in other words the smallest discernible feature that can be resolved by the AFM. According to embodiments the lateral resolution may also be denoted as spatial resolution.

The step of resolving the one or more geometric parameters may involve quantifying the size distribution of detected amyloid aggregates with nanometer scale spatial resolution.

Hence methods according to embodiments of the invention include a detailed analysis and imaging of detected amyloid aggregates.

According to embodiments the analysis targets and focuses on the detection and then the further detailed analysis/imaging of the amyloid aggregates as such and not on the resolution and imaging of the overall shape of red blood cells.

According to an embodiment, the providing of the blood sample comprises passivating the blood sample with a passivation layer, wherein the passivation layer comprises a first material.

According to embodiments, the blood sample comprises the passivation layer during the performing of the analysis of the blood sample.

Such a passivation layer facilitates the imaging and detection of the amyloid aggregates in the surface layer of the blood sample. On the one hand, the passivation layer may prevent or at least reduce ambient contaminations of the surface layer of the blood sample. On the other hand, the passivation layer may increase the imaging stability of the atomic force microscope.

More particularly, the passivation layer may be embodied as a liquid layer. During the analysis of the surface, the tip of the atomic force microscope immerses into the liquid layer and the surface of the blood sample underlying the liquid layer is analyzed. More particularly, methods according to embodiments of the invention do not analyze the liquid layer which surrounds the red blood cells, in particular not the surface of the liquid layer, but they analyze directly the surface of the red blood cells which is below, behind or in other words underlies the liquid layer. Accordingly the tip of the AFM touches directly the surface of the red blood cells while being stabilized by the surrounding liquid of the liquid layer. Hence the liquid layer is configured to stabilize the tip movement during the analysis, thereby increasing the imaging stability of the atomic force microscope.

In other words, such a liquid layer facilitates an immersion of the tip of the atomic force microscope into the liquid layer as well as a stabilization of the tip by the liquid surrounding the immersed tip. This further increases the image stability and facilitates to obtain very high-resolution images of the red blood cells without destroying the delicate cell membrane.

More particularly, such a thin liquid encapsulation of the blood sample by the liquid layer prevents the formation of a liquid bridge at the nanoscopic contact between the AFM tip and the surface of the blood sample, thereby improving the stability during AFM imaging.

According to an embodiment, the liquid layer has a kinematic viscosity between 100 centistokes (cSt) and 1000 centistokes (cSt). Such a kinematic viscosity shows a particularly advantageous stabilization of the AFM-tip.

According to an embodiment, the first material of the passivation layer is liquid silicone.

The liquid silicone may be in particular embodied as silicone oil. According to embodiments, silicone oil with the CAS-number 63148-62-9 and the linear formula $[-Si(CH3)_2O-]_n$ may be used.

According to embodiments, the passivation layer, in particular the layer of liquid silicone, may be applied by spray coating.

According to an embodiment, the passivation layer has a thickness between 0.5 μm and 2 μm. Such dimensions provide advantageous imaging stability.

According to an embodiment of the invention, the method further comprises steps of resolving edges of one or more red blood cells in the surface layer of the blood sample and performing one or more scans of the surface of the one or more red blood cells by operating a tip of the atomic force microscope at the one or more resolved red blood cells to detect amyloids which may have been aggregated on the surface of the red blood cells.

Such a two-stage operation of the atomic force microscope facilitates an efficient imaging and detection of amyloid aggregates. At a first stage, the atomic force microscope is operated to detect and resolve the edges of the one or more red blood cells in the surface layer of the blood sample. Then, at a second stage, the atomic force microscope is operated only at the detected and resolved red blood cells.

According to an embodiment of the invention, the method further comprises steps of resolving edges of one or more red blood cells in the surface layer of the blood sample and performing an analysis of an edge layer of the one or more resolved red blood cells by operating the tip of the atomic force microscope at the edge layer of the one or more resolved red blood cells to detect amyloid aggregates in the edge layer of the red blood cells.

According to such an embodiment, the atomic force microscope is used to perform only or in particular an analysis of the edge layer of the red blood cells. Such an edge layer, which may also be denoted as peripheral layer, is a surface layer which is situated at the edge of the red blood cells. The red blood cells have a biconcave structure, wherein the thickness of the red blood cells is higher at the edge than in the center. Red bloods cells have typically a lateral extension/diameter of 6.2 µm to 8.2 µm, a maximum thickness or height of 2 µm to 2.5 µm and a minimum thickness or height of 0.8 µm to 1 µm.

Focusing on the edge layer of the red blood cells is counterintuitive, as it is much more difficult to operate the AFM at the edges of the red blood cells. More particularly, the tip-surface interactions are more unstable as the tip may slip from the interface due to height differences. Furthermore, the edge of red blood cells has a curvature whose sides cannot be resolved by the AFM tip. However, it may facilitate the early detection of amyloid aggregates. More particularly, the inventor of the present invention has discovered that at early stages of neurodegenerative diseases the amyloids aggregate at the edges of the red blood cell, but not or to a lower extent in the center.

According to an embodiment, the edge layer may encompass a radial outer layer of the blood cells. According to embodiments, the edge layer has a radial extension or thickness between 10% and 50% of the radius of the red blood cell, in particular between 20% and 30%. As an example, for a red blood cell with a radius of 3 µm, the edge layer may have a radial extension between 1.5 µm and 0.3 µm, in particular between 0.6 µm and 0.9 µm.

According to an embodiment, the method further comprises performing a statistical analysis of height and phase (contrast) images to quantify the size, shape and/or the morphology of resolved amyloid aggregates.

Such a post-processing of the height and phase contrast images may provide additional details of the detected amyloid aggregates.

According to an embodiment, the method further comprises operating the atomic force microscope in peak force mode. This provides an advantageous resolution and detection of the amyloid aggregates.

However, according to further embodiments the atomic force microscope may also be operated in other modes, e.g. in traditional tapping or contact mode.

According to an embodiment, the method further comprises operating the atomic force microscope with a loading force between 0.5 nN and 1 nN.

Such forces optimize the interaction between the atomic force microscope tip and the red blood cells. This facilitates an advantageous resolution and detection of the amyloid aggregates.

According to an embodiment, the blood sample comprises or consists of dried blood. This facilitates an efficient and reliable sample preparation and handling. Dried blood samples may be fixed e.g. on a clean glass slide. Furthermore, a dried blood sample facilitates the application of the passivation layer. The dried blood sample may be in particular embodied as blood smear.

However, according to other embodiments, also fluid blood or purified red blood cells may be used.

The atomic force measurements can be conducted according to embodiments on small blood samples encompassing quantities between 1 µL and 5 µL.

According to an embodiment, the blood sample comprises human blood. Such an embodiment may be in particular used for the early detection of neurodegenerative human diseases such as Alzheimer.

However, according to other embodiments, also the blood of animals may be analyzed.

According to an embodiment of another aspect of the invention, an atomic force microscope is provided. The atomic force microscope is configured to perform an automated and/or semi-automated analysis of a surface layer of a blood sample to detect amyloid aggregates on red blood cells of the blood sample. The analysis includes an (direct) imaging of detected amyloid aggregates. The automated and/or semi-automated analysis may be facilitated by control programs or computer program products. According to embodiments the atomic force microscope may use artificial intelligence for the automated/and or semi-automated analysis of the surface layer of the blood sample. The artificial intelligence may be trained according to embodiments for the detection of amyloid aggregates.

According to an embodiment of another aspect of the invention, a computer program product for operating an atomic force microscope is provided. The computer program product comprises a computer readable storage medium having program instructions embodied therewith. The program instructions are executable by the atomic force microscope to cause the atomic force microscope to perform a method comprising performing an analysis of a surface layer of a blood sample to detect amyloid aggregates by atomic force microscopy. The method includes an (direct) imaging of the detected amyloid aggregates.

An embodiment of another aspect of the invention relates to the use of an atomic force microscope for the detection of amyloid aggregates in a blood sample.

Features and advantages of one aspect of the invention may be applied to the other aspects of the invention as appropriate.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein:

FIG. 6b shows a zoom in height image over the black box shown in FIG. 6a;

FIG. 6c shows a high-resolution height image acquired over several samples on the resolved red blood cell 30 of FIG. 6a; and FIG. 6d shows another high-resolution height image acquired over several samples on the resolved red blood cell 30 of FIG. 6a.

MODES FOR CARRYING OUT THE INVENTION

At first, some general aspects and terms of embodiments of the invention will be introduced.

The terms amyloids or amyloid aggregates may denote according to embodiments of the invention amyloid peptides as well as amyloid proteins. The term shall encompass tau proteins and alpha-synucleins. According to embodiments amyloids or amyloid aggregates may encompass or may be defined as aggregates of proteins and/or peptides having a spherical and/or fibrillary morphology or fibrillar structure and comprising in particular oligomers from 3 nm-15 nm in diameter and fibrils of 6 nm-15 nm in diameter and a β-sheet secondary structure or in other words cross-β structure. Furthermore, fibrils may have an ability to be stained by particular dyes, such as Congo red.

The term amyloid aggregates shall encompass oligomers, protofibrils as well as mature fibrils.

In any or all of the figures the dimensions may not be drawn to scale and may be shown in a simplified and schematic way to illustrate the features and principles of embodiments of the invention.

Figure 1:
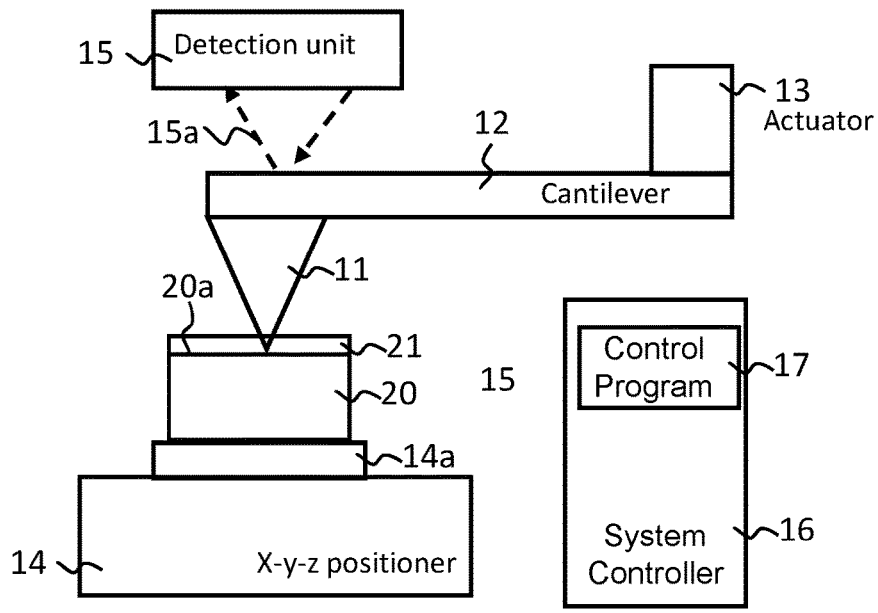
FIG. 1 shows an exemplary block diagram of a measurement arrangement comprising an atomic force microscope according to an embodiment of the invention.

FIG. 1 shows an exemplary block diagram of a measurement arrangement comprising an atomic force microscope 10 according to an embodiment of the invention.

The atomic force microscope 10 is configured to perform an analysis of a blood sample 20 to detect amyloid aggregates in red blood cells of the blood sample 20. According to embodiments the atomic force microscope 10 may perform an automated and/or semi-automated imaging and detection of the amyloid aggregates in the blood sample 20.

The atomic force microscope 10 comprises a tip 11, which may also be denoted as probe tip 11. The tip 11 is arranged on a free end of a cantilever 12. The apex of the tip 11 is preferably less than 5 nm and accordingly it may be in particular embodied as ultra-sharp tip. The cantilever 12 may be actuated by an actuator 13. The actuator 13 may be in particular arranged opposite to the free end of the cantilever 12. The actuator 13 may be embodied as piezoelectric actuator. According to embodiments, the actuator 13 may oscillate the cantilever 12, in particular the tip 11, in a vertical z-direction.

The atomic force microscope 10 further comprises a x-y-z positioner unit 14 with a probe table 14a. The positioner unit 14 may move and position the probe table 14a in a horizontal plane corresponding to the x-direction and the y-direction as well as in a vertical z-direction.

On the probe table 14a is arranged a blood sample 20. The blood sample 20 is covered by a passivation layer 21.

The atomic force microscope 10 further comprises a detection unit 15 for detection of a deflection and motion of the cantilever 12. The detection unit 15 may encompass e.g. a laser unit for generating a laser beam 15a and an optical sensor for detecting the deflected laser beam 15a.

Furthermore, the atomic force microscope 10 comprises a system controller 16 which is configured to control the operation of the atomic force microscope 10. The system controller 16 comprises a control program 17 comprising program code for the control and operation of the atomic force microscope 10. The control program 17 may comprise a computer program product for operating the atomic force microscope 10. The control program 17 may facilitate an automated/and or semi-automated analysis of the surface layer of the blood sample 20. The control program 17 may comprise in particular encoded artificial intelligence such as machine learning algorithms for pattern recognition for the detection of amyloid aggregates in blood samples.

Figure 2:
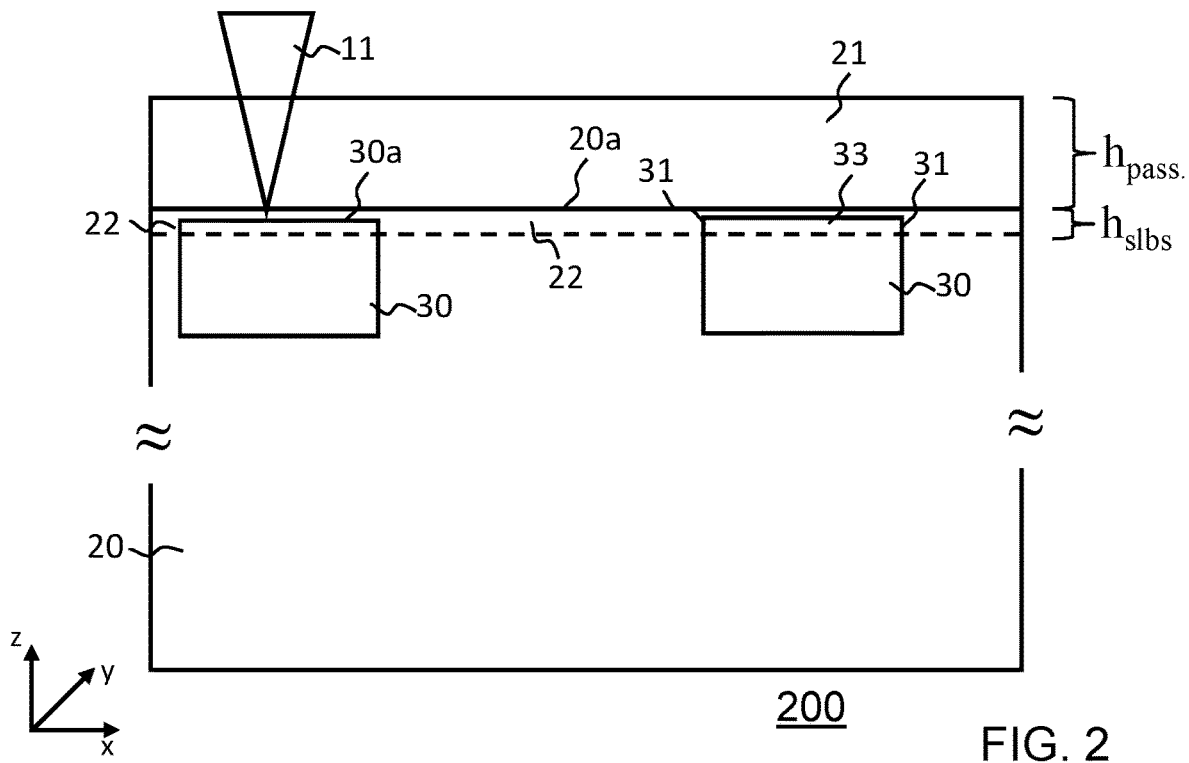
FIG. 2 shows an enlarged cross-sectional view of a blood sample, a probe tip 11 and a passivation layer.

FIG. 2 shows an enlarged cross-sectional view or side view of the blood sample 20, the probe tip 11 and the passivation layer 21. The passivation layer 21 may be in particular embodied as a liquid layer. The liquid layer may preferably have a kinematic viscosity between 100 centistokes (cSt) and 1000 cSt. The passivation layer 21 comprises or consists of a first material, e.g. of liquid silicone. The passivation layer is preferably embodied as thin layer having a thickness or height $h_{pass}$ between 0.5 μm and 2 μm. Such a thickness is ideal for immersing the tip 11 into the passivation layer 21 and for providing improved imaging stability.

The scanning probe microscope 10 performs an analysis of a surface layer 22 of the blood sample 20. The surface layer 22 which is subject to the detailed AFM analysis may have a thickness or height $h_{slbs}$ of e.g. 100 nm. The blood sample 20 comprises a plurality of red blood cells 30 (in this exemplary figure represented in a simplified manner by a rectangular cross section). Some of the red blood cells are arranged at the surface of the blood sample 20 and in particular at least partly in the surface layer 22 of the blood sample 20. The part of the red blood cell that is arranged in the surface layer 22 of blood sample 20 is in particular analyzed and imaged by the atomic force microscope 10 to detect amyloid aggregates and may be denoted as surface layer 33 of the red blood cells 30. The surface layer 33 of the red blood cells 30 which is subject to a detailed AFM analysis may have a thickness or height of e.g. 100 nm.

Figure 5:
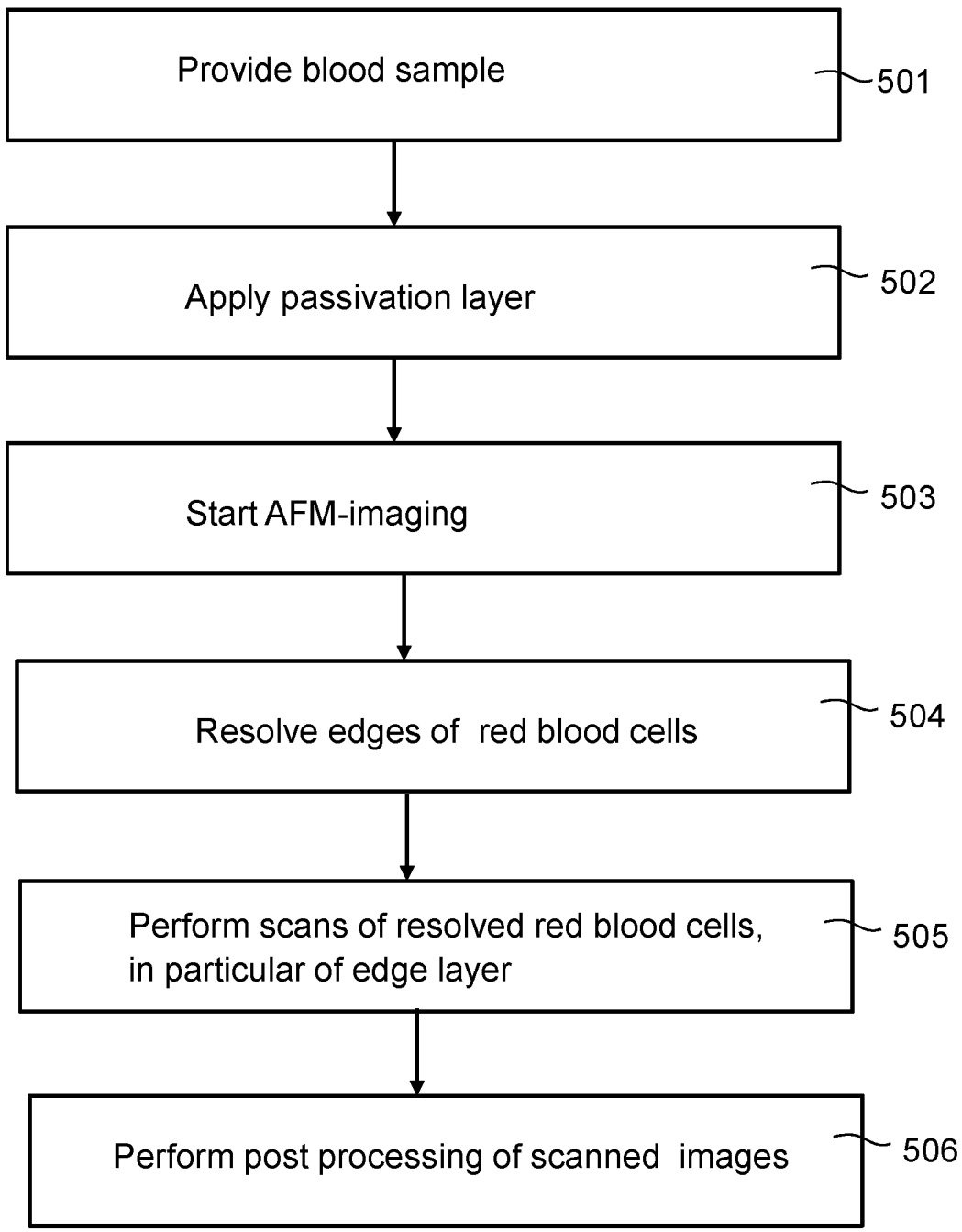
FIG. 5 shows a flow chart of method steps of a method for imaging and detecting amyloid aggregates in blood.

Referring now to FIG. 5, a flow chart of method steps of a method for imaging and detecting amyloid aggregates in blood will be explained. The method can be performed by the atomic force microscope 10 of FIG. 1 and hence in the following explanation of the method it will be referred to the components of FIGS. 1 and 2.

At a step 501, the blood sample 20 is provided. The blood sample 20 may be in particular a dried blood sample of a blood smear and may be fixed e.g. on a clean glass slide. The measurements and analysis of the dried blood sample 20 can be conducted on small blood sample quantities of e.g. 1 μL to 5 μL.

According to other embodiments the blood sample 20 may be a fluid blood sample or a blood sample comprising purified red blood cells. Purified red blood cells may have been derived from an original blood sample by centrifugation.

At a step 502, the passivation layer 21 is applied to the blood sample 20. In other words, the blood sample 20 is coated with the passivation layer 21. The coating of the dried blood sample 20 may be performed using spray coating, e.g. by spray coating of liquid silicone with a viscosity range from 100 to 1000 cst.

At a step 503, the imaging of the AFM starts. This includes to immerse the tip 11 into the passivation layer 21. The thin liquid encapsulation of the tip 11 by the passivation layer 21 prevents the formation of a liquid bridge at the nanoscopic contact between the tip 11 and the surface 20a of the blood sample 20. This improves the stability during the AFM imaging.

The mode in which the AFM is operated ensures that the force between the blood sample 20 and the tip 11 is well controlled. The adjustable tip-sample forces can be modulated to ensure that height and phase contrast images can be extracted and overlayed. According to embodiments a force constant of 2 N/m and a loading force for best resolution between 0.5 and 1 nN may be used. The apex of the tip 11 is preferably less than 5 nm.

More particularly, according to embodiments the tip 11 is oscillated vertically in the z-direction near its mechanical resonance frequency. As the tip 11 lightly taps the surface 20a of the blood sample 20, the amplitude of oscillation is reduced and the AFM 10 uses this change in amplitude in order to image the surface topography of the blood sample 20, thereby generating a height image.

In addition to its amplitude, the motion of the tip 11 can be characterized by its relative phase with respect to a driving oscillator of the actuator 13. Such changes of the relative phase may generate phase images of the blood sample 20.

According to preferred embodiments, the AFM 10 is operated in peak force mode. According to other embodiments, the AFM 10 may also be operated in tapping or contact mode.

After engaging the AFM tip 11 on the surface 20a of the blood sample 20, the (lateral) edges 31 of the red blood cells 30 which are situated in the surface layer 22 of the blood sample 20 are at first detected and resolved.

Figure 3:
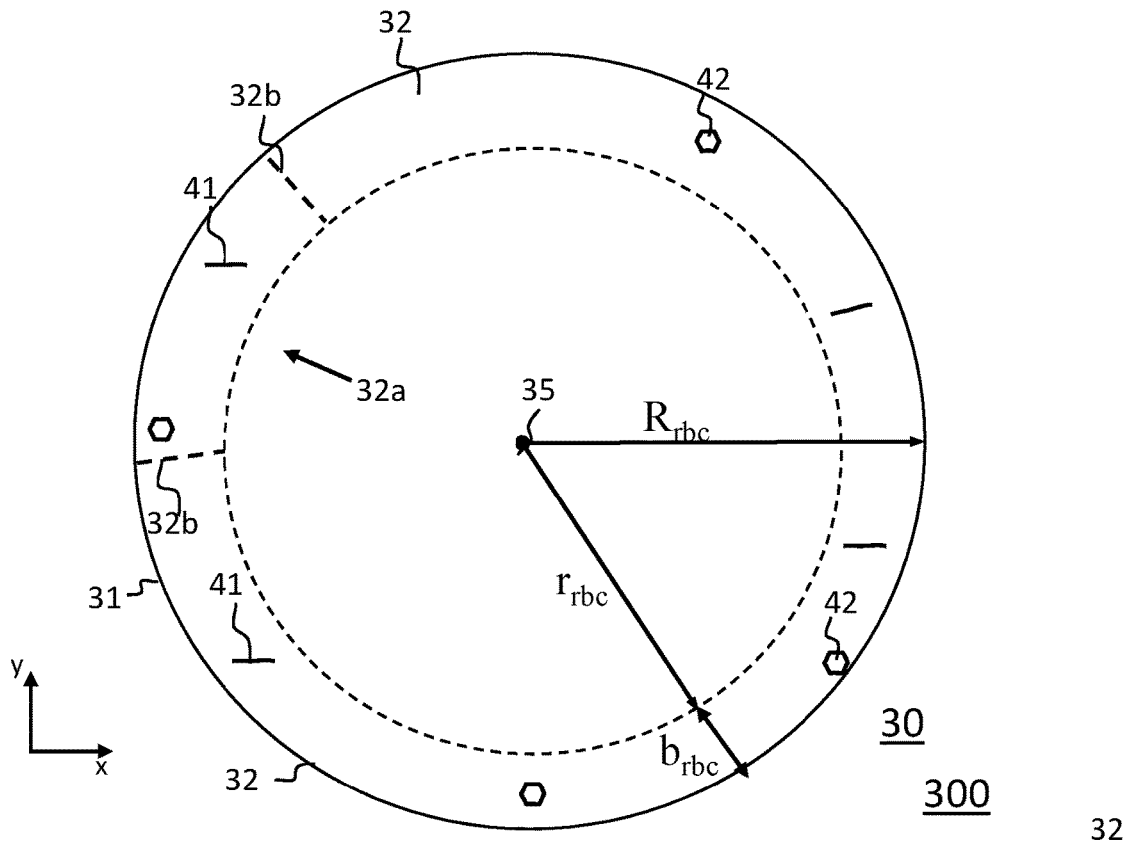
FIG. 3 shows an enlarged top view of a red blood cell.
Figure 4:
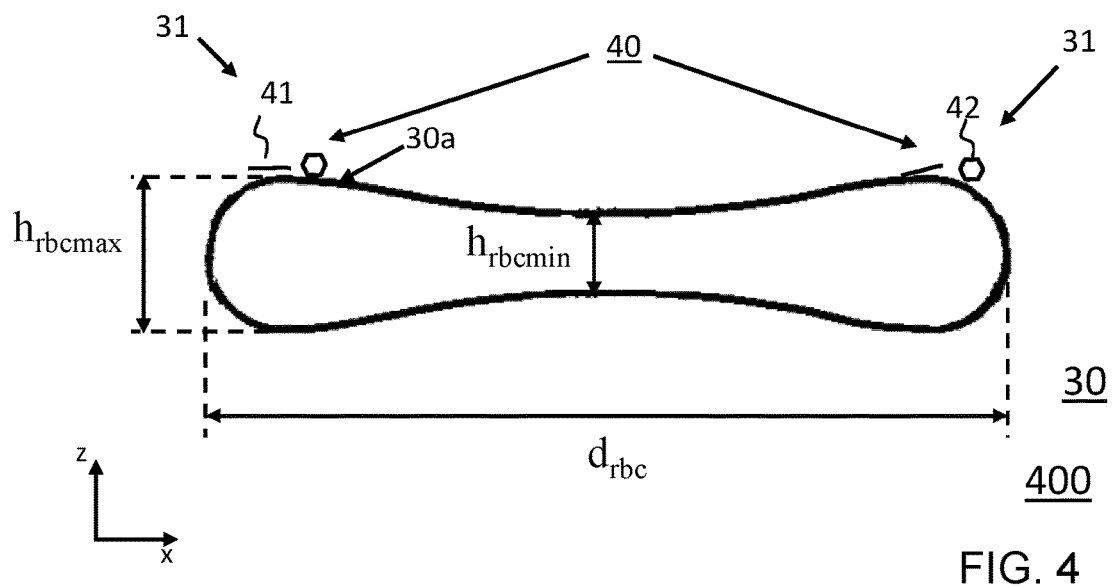
FIG. 4 shows a corresponding side view or cross sectional view of the red blood cell of FIG. 3.

FIG. 3 shows an enlarged 3-dimensional view 300 of a red blood cell 30. FIG. 4 shows a corresponding side view or cross sectional view 400 of the red blood cell 30.

According to this example it is assumed that the red blood cell 30 comprises two types of amyloid aggregates, namely fibrils 41 and oligomers 42, which are collectively referred to as amyloid aggregates 40.

During the step 504, the AFM 30 has resolved the amyloid aggregates 40 which are situated in the surface layer 33 of the red blood cell 30, in particular the lateral edges 31 of the red blood cells 30.

Then, at a step 505, the tip 11 is operated at the respective resolved red blood cell 30, in particular at the edges 31, in particular at an edge layer 32 of the respective red blood cell 30. This step 505 may encompass one or more scans or runs The edge layer 32 is a peripheral layer of the surface of the red bloods cells which is located at or close to the edge 31 of the red blood cells 30. The red blood cells 30 have a biconcave structure as illustrated in FIG. 4. The red blood cells 30 have typically a size of 6.6 to 8.2 microns in diameter $d_{rbc}$ and a maximum thickness or height $h_{rbcmax}$ between 2 microns and 2.5 microns.

The thickness or height $h_{rbc}$ in the z-direction of the red blood cells 30 is higher at the edges 31 than in the center 35 of the red blood cells 30. The red blood cells 30 have typically a minimum thickness or height $h_{rbcmin}$ between 0.8 microns and 1 micron in the center of the red blood cell.

According to embodiments the tip 11 of the AFM 30 is operated in particular at the peripheral area of the red blood cells which has a higher thickness in the z-direction. According to embodiments, the tip 11 of the AFM is operated in particular at the surface area of the red blood cells 30 which has a height $h_{rbc}$ of more than 1.5 μm, and more preferably a height $h_{rbc}$ of more than 1.7 μm. According to such an embodiment the edge layer 32 may be defined as the surface area of the red blood cell 30 which has a height $h_{rbc}$ of more than 1.5 μm, and more preferably a height $h_{rbc}$ of more than 1.7 μm.

As shown in FIG. 3, the edge layer 32 may also be defined according to embodiments as a radial outer layer of the red blood cell 32.

According to embodiments, the edge layer has a radial thickness or radial extension $b_{rbc}$ between 10% and 50% of the outer radius $R_{rbc}$ of the red blood cell 30, in particular between 20% and 30% of the radius $R_{rbc}$. The radial extension $b_{rbc}=R_{rbc}-r_{rbc}$, wherein $r_{rbc}$ is the inner radius of the edge layer 32. The (fictive) inner radius $r_{rbc}$ of the edge layer 32 is illustrated with a dotted circle.

Operating the AFM 30 at the edge or in other words on the edge layer 32 of the red blood cell 30 is in particular challenging, but it may facilitate the early detection of amyloid aggregates. More particularly, the inventor of the present invention has discovered that at early stages of neurodegenerative diseases the amyloids may aggregate only at the edges of the red blood cell 30, but not or to a lower extent in the center, as illustrated also in FIG. 3 and FIG. 4.

Such an analysis of the edge layer 32 may be limited to the analysis of a part or section of the edge layer. Referring to FIG. 3, the AFM tip may be operated e.g. only at a part 32a of the edge layer 32 which is confined by dotted lines 32b.

During step 505 the amyloid aggregates 40, in particular the amyloid aggregates in the edge layer 32, may be imaged, resolved and detected. The step 505 may generate in particular height images and phase contrast images of the surface 30a of the red blood cells 30.

After resolving the amyloid aggregates 40 or in other words the amyloid aggregates 40, a post processing of the scanned images which have been generated at step 505 may be performed at step 506. This post processing may include in particular to perform a statistical analysis of the height and phase contrast images. Such a post-processing may allow to quantify the size, shape and morphology of the resolved amyloid aggregates 40.

With such a method a reliable test to confirm the presence or absence of nanostructured sized amyloid aggregates may be established. Such aggregated amyloids are the pathological hallmark of various neurodegenerative diseases such as Alzheimer's, Parkinson's, Neuroferritinopathy, Dementia with Lewy bodies, Huntington disease, Lysozyme amyloidosis, Familial British dementia, Spinocerebellar ataxis and Familial Danish Dementia.

FIGS. 6a to 6d show as experimental evidence real AFM images of amyloid aggregates resolved in human blood which have been generated by a method according to an embodiment of the invention. The AFM images have been generated by an atomic force microscope operated in peak force mode. More particularly, the measurement was done using a Multimode AFM 8 tool of Bruker Corporation. Blood smear on glass slides was used as blood sample. All the AFM measurements were conducted under standard laboratory conditions.

Figure 6A:
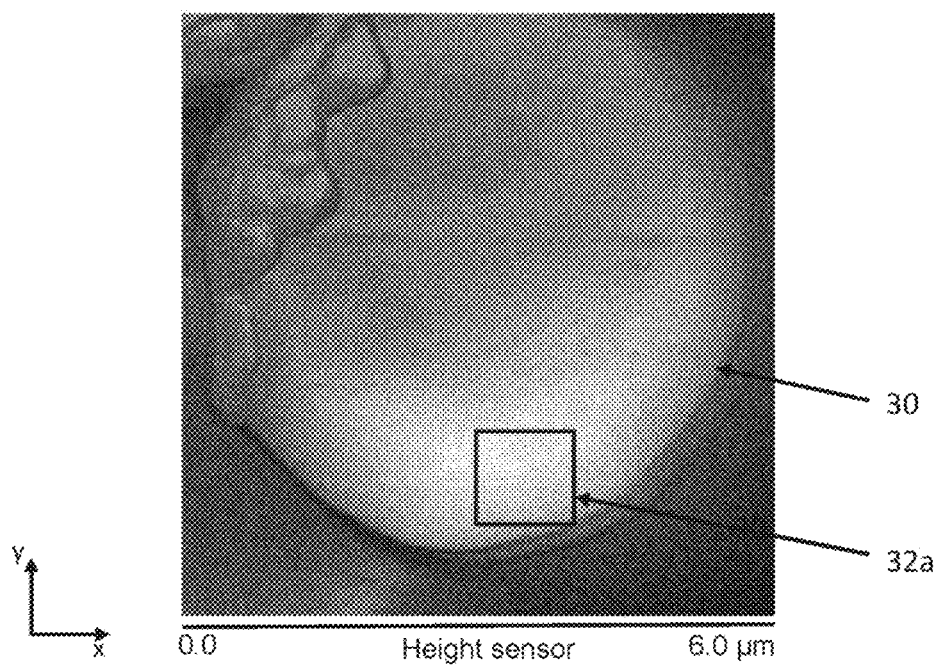
FIG. 6a shows a height image of a red blood cell provided by a height sensor of an atomic force microscope.

FIG. 6a shows a height image 601 of a red blood cell 30 provided by a height sensor of the atomic force microscope 10. The AFM image 601 was taken from a red blood cell of a blood sample which was encapsulated/covered by viscous liquid silicone.

Figure 6B:
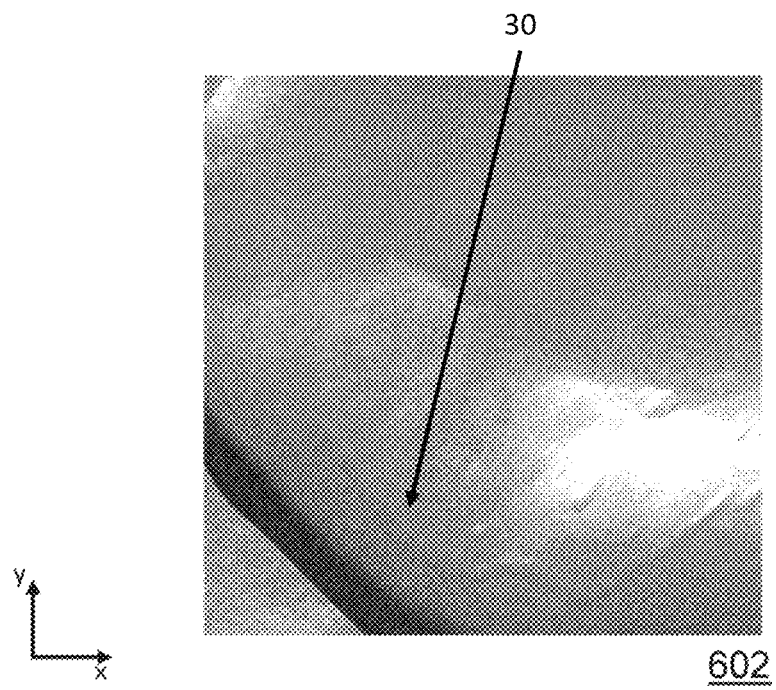

FIG. 6b shows a zoom in height image over the black box 32a shown in FIG. 6a, representing an edge area or in other words a part or section of the edge layer of the red blood cell 30 that has been analyzed in more detail.

Figure 6C:
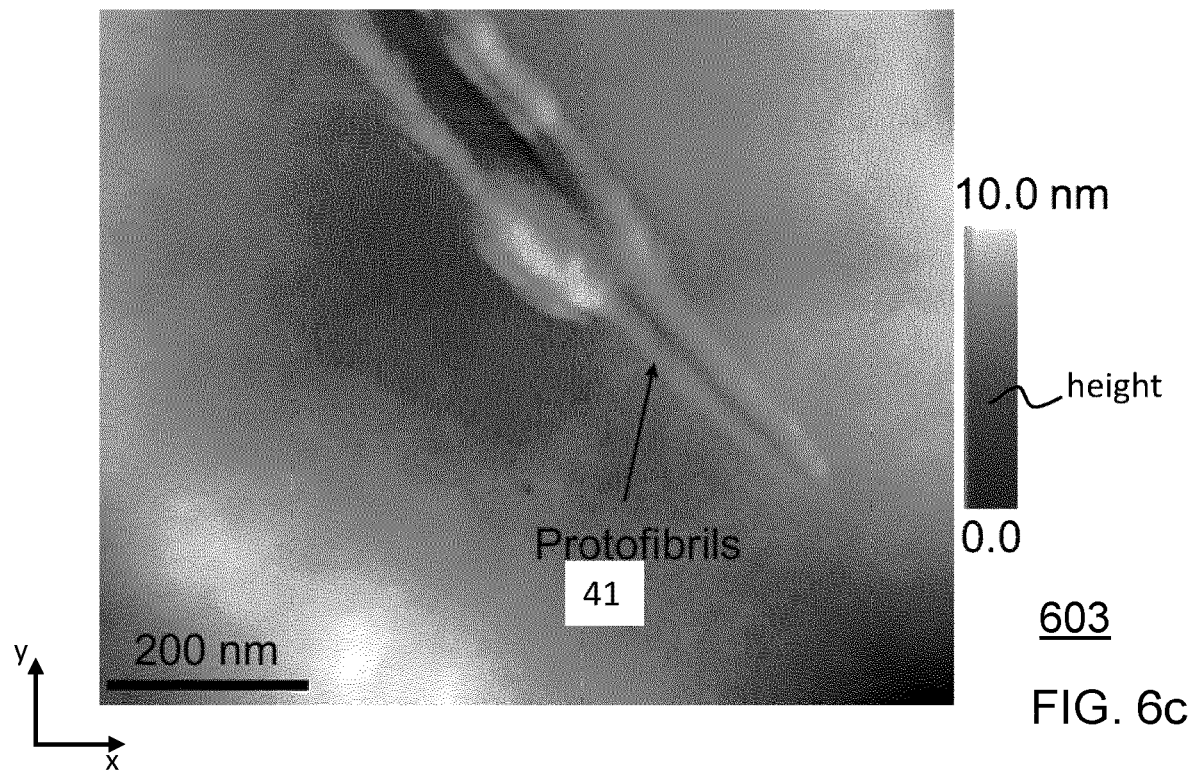

FIG. 6c shows a high-resolution height image acquired over several samples on the resolved edge area of the red blood cell 30 of FIG. 6b. The atomic force microscopy has imaged and detected as amyloid aggregates protofibrils 41.

The height is gray-scale coded.

Figure 6D:
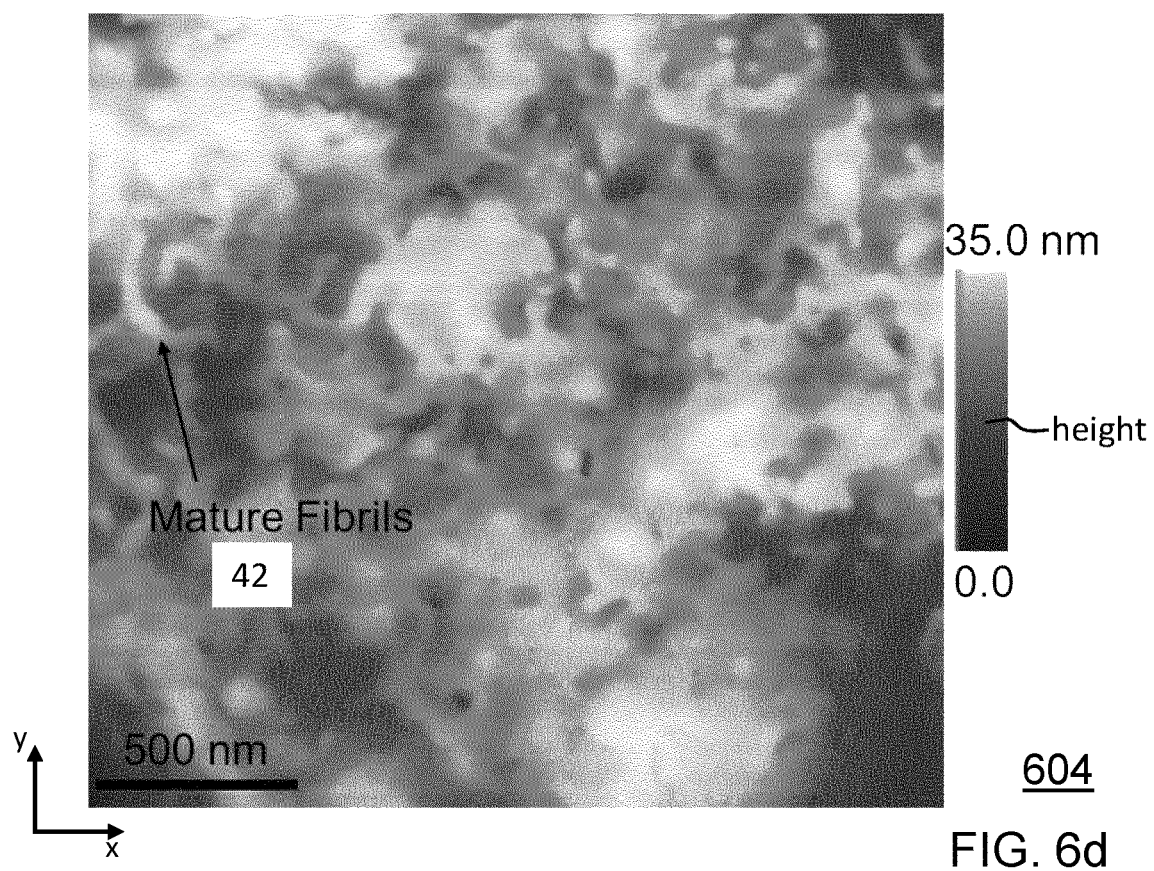

FIG. 6d shows another high-resolution height image acquired over several samples on the resolved edge area of the red blood cell 30 of FIG. 6b. The atomic force microscope imaged and detected as amyloid aggregates 40 mature fibrils 42.

The height is gray-scale coded.

Aspects of the present invention may be embodied as a measurement system comprising an atomic force microscope, a method, a computer program product as well as a new use of an atomic force microscope. The computer program product may include a computer readable storage medium (or media) having computer readable program instructions thereon for causing a processor to carry out aspects of the present invention.

Computer readable program instructions described herein can be downloaded to respective computing/processing devices from a computer readable storage medium or to an external computer or external storage device via a network, for example, the Internet, a local area network, a wide area network and/or a wireless network.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages.

Computer readable program instructions according to embodiments of the invention may be provided to a system controller of a measurement system, in particular to a system controller of an atomic force microscope.

While there are shown and described presently preferred embodiments of the invention, it is to be distinctly understood that the invention is not limited thereto but may be otherwise variously embodied and practiced within the scope of the following claims.

The invention claimed is:

1. A method for detecting amyloid aggregates in blood, the method comprising
providing a blood sample comprising one or more red blood cells; and
performing an analysis of a surface layer of the blood sample by an atomic force microscope to detect amyloid aggregates on a surface of the one or more red blood cells; and
imaging detected amyloid aggregates.

2. A method according to claim 1, further comprising quantifying the size, shape and/or the morphology of detected amyloid aggregates.

3. A method according to claim 1, further comprising imaging detected amyloid aggregates with varying size and shapes.

4. A method according to claim 1,
wherein the detected amyloid aggregates encompass tau proteins and/or alpha-synucleins.

5. A method according to claim 1, further comprising resolving one or more geometric parameters of detected amyloid aggregates.

6. A method according to claim 5, wherein the step of resolving the one or more geometric parameters involves a quantification of the one or more geometric parameters on a nanometer scale.

7. A method according to claim 5, wherein the one or more geometric parameters encompass the size, shape and/or morphology of detected amyloid aggregates.

8. A method according to claim 1, wherein the providing of the blood sample comprises passivating the blood sample with a passivation layer, the passivation layer comprising a first material; and
wherein the blood sample comprises the passivation layer during the performing of the analysis of the blood sample.

9. A method according to claim 8, wherein
the atomic force microscope comprises a tip and the passivation layer is embodied as a liquid layer, wherein the tip immerses into the liquid layer during the analysis to analyze the surface of the blood sample underlying the liquid layer, wherein the liquid layer is configured to stabilize the tip movement during the analysis, thereby increasing the imaging stability of the atomic force microscope.

10. A method according to claim 9, wherein the liquid layer has a kinematic viscosity between 100 cSt and 1000 cSt.

11. A method according to claim 8, wherein the first material is liquid silicone, in particular silicone oil.

12. A method according to claim 8, wherein the passivation layer has a thickness between 0.5 μm and 2 μm.

13. A method according to claim 1, further comprising resolving edges of one or more red blood cells in the surface layer of the blood sample; and
performing one or more scans of the one or more red blood cells by operating a tip of the atomic force microscope at the one or more resolved red blood cells to detect amyloid aggregates on the one or more red blood cells.

14. A method according to claim 1, further comprising resolving edges of one or more red blood cells in the surface layer of the blood sample; and
performing an analysis of an edge layer of the one or more resolved red blood cells by operating the tip of the atomic force microscope at the edge layer of the one or more resolved red blood cells to detect amyloid aggregates in the edge layer of the red blood cells.

15. A method according to claim 1, further comprising performing a statistical analysis of height and phase contrast images; and quantifying the size, shape and/or the morphology of resolved amyloid aggregates.

16. A method according to claim 1, further comprising operating the atomic force microscope in peak force mode.

17. A method according to claim 1, further comprising operating the atomic force microscope with a loading force between 0.5 nN and 1 nN.

18. A method according to claim 1, wherein the blood sample comprises dried blood.

19. A method according to claim 1, wherein the blood sample-comprises human blood.

20. An atomic force microscope, the atomic force microscope being configured to perform an automated and/or semi-automated analysis of a surface layer of a blood sample to detect amyloid aggregates on red blood cells of the blood sample, the analysis comprising imaging detected amyloid aggregates.

21. A computer program product for operating an atomic force microscope, the computer program product comprising a computer readable storage medium having program instructions embodied therewith, the program instructions executable by the atomic force microscope to cause the atomic force microscope to perform a method comprising
performing an analysis of a surface layer of a blood sample to detect amyloid aggregates by atomic force microscopy; and
imaging detected amyloid aggregates.

* * * * *